(12) United States Patent
Bohmer

(10) Patent No.: US 6,617,158 B1
(45) Date of Patent: Sep. 9, 2003

(54) METHOD FOR STIMULATING THE PRODUCTION OF FETAL HEMOGLOBIN PRODUCING ERYTHROID CELLS

(75) Inventor: Ralph M. Bohmer, Brookline, MA (US)

(73) Assignee: New England Medical Center, Boston, MA (US)

( * ) Notice: Subject to any disclaimer, the term of this patent is extended or adjusted under 35 U.S.C. 154(b) by 0 days.

(21) Appl. No.: 09/637,539

(22) Filed: Aug. 11, 2000

Related U.S. Application Data

(60) Provisional application No. 60/149,815, filed on Aug. 19, 1999.

(51) Int. Cl.⁷ .............................. C12N 5/00; C12N 5/02; C12Q 1/00; C07K 2/00; C07K 14/00
(52) U.S. Cl. .......................... 435/325; 435/4; 435/372; 435/375; 435/383; 435/384; 435/395; 530/300; 530/350
(58) Field of Search ............................ 435/4, 325, 372, 435/375, 383, 384, 395

(56) References Cited

U.S. PATENT DOCUMENTS

| | | | | |
|---|---|---|---|---|
| 5,192,553 | A | 3/1993 | Boyse et al. | 424/529 |
| 5,366,996 | A | 11/1994 | Elford et al. | 514/575 |
| 5,700,640 | A | 12/1997 | Voss et al. | 435/6 |

FOREIGN PATENT DOCUMENTS

| | | |
|---|---|---|
| WO | WO 95/26507 | 10/1995 |

OTHER PUBLICATIONS

Bohmer et al. Differential development of fetal and adult haemoglobin profiles in colony culture: isolation of fetal nucleated red cells by two–colour fluorescence labelling. Br J Haematol 103(2):351–360, 1998.*
Kystal et al. Transforming growth factor beta 1 is an inducer of erythroid differentiation. J Exp Med. 180(3):851–860, 1994.*
Mayani et al. Differential effects of the hematopoietic inhibitors MIP–1 alpha, TGF–beta, and TNF–alpha on cytokine–induced proliferation of subpopulations of CD34+ cells purified from cord blood and fetal liver. Exp Hematol. 23(5):422–427, 1995.*
Zermati et al. TGF–beta1 drives and accelerates erythroid differentiation in the epo–dependent UT–7 cell line even in the absence of erythropoietin. Exp Hematol. 28(3):256–266, 2000.*
Callard and Gearing. The Cytokine FactsBook. London: Academic Press, 1994; p. 235.*
Bohmer RM, "Two–step cell–death kinetics in vitro during cis–platinum, hydroxyurea and mitomycin incubation." Cell Tissue Kinet, Nov. 1994; 17(6):593–600.

Bohmer RM, "Flow cytometric cell cycle analysis using the quenching of 33258 Hoechst fluorescence by bromodeoxyuridine incorporation." Cell Tissue Kinet, Jan. 1979; 12(1):101–10.
Bohmer RM et al., "Selectively increased growth of fetal hemoglobin–expressing adult erythroid progenitors after brief treatment of early progenitors with transforming growth factor beta." Blood, May 1, 2000; 95(9):2967–74.
Jane SM et al., "Understanding fetal globin gene expression: a step towards effective HbF reactivation in haemoglobinopathies." Br J Haematol, Jul. 1998; 102(2):415–22.
Bohmer RM et al., "Identification of fetal nucleated red cells in co–cultures from fetal and adult peripheral blood: differential effects of serum on fetal and adult erythropoiesis." Prenat Diagn, Jul. 1999; 19(7):628–36.
Papayannopoulou T et al., "Erythroid progenitors circulating in the blood of adult individuals produce fetal hemoglobin in culture." Science, Mar. 24, 1978; 199(4335):1349–50.
Epstein FH et al., "Pathogenesis and treatment of sickle cell disease." The New England Journal of Medicine, Sep. 11, 1997; 762–769.
Pembrey ME et al., "Fetal haemoglobin production and the sickle gene in the Oases of Eastern Saudi Arabia." British Journal of Haematology, 1978, 40, 415–429.
Gabbianelli, M., et al., "Reactivation of HbF synthesis in normal adult erythroid bursts by IL–3." British Journal of Haematology, Jan. 1990, 74(1):114–117.
Umemura, T., et al., "Effects of Interleukin–3 and Erythropoietin on In Vivo Erythropoieses and F–Cell Formation in Primates." Blood, Oct. 1989, 74(5):1571–1576.
Fibach, E., "Techniques for Studying Stimulation of Fetal Hemoglobin Production in Human Erythroid Cultures." Hemoglobin, 1998; 22(5&6):445–458.

(List continued on next page.)

Primary Examiner—Elizabeth Kemmerer
Assistant Examiner—Bridget E. Bunner
(74) Attorney, Agent, or Firm—Mintz, Levin, Cohn, Ferris, Glovsky and Popeo, P.C.; Ingrid A. Beattie

(57) ABSTRACT

The present invention provides a method for ameliorating β-globin disorders in a mammal. In one aspect of the invention, the treatment involves ex vivo treatment of early erythroid progenitor cells that leads to an increase in the relative amounts of cells subsequently expressing and accumulating HbF. The cell treatment is to be followed by transplantation of the modified cells. In another aspect of the invention, the same modification of progenitor cells occurs in vivo. Both treatments are based on the novel discovery that the modification can be performed very early in the erythroid maturation process, without disturbance of the subsequent proliferation and maturation of the erythroid precursor. The present invention also provides a procedure for the monitoring of β-globinopathies and the response of a patient to treatment. In this aspect of the invention, erythropoiesis of a patient is studied (in vivo or in vitro) by generating profiles of correlated contents of different types of hemoglobin present in nucleated red cells.

5 Claims, 11 Drawing Sheets

OTHER PUBLICATIONS

Shao, L., et al., "Effect of Activin A on Globin Gene Expression in Purified Human Erythroid Progenitors." Blood, Feb. 1992; 79(3):773–781.

Croizat, H., and Nagel, R., "Circulating Cytokines Response and the Level of Erythropoiesis in Sickle Cell Anemia." American Journal of Hematology, Feb. 1999; 60(2):105–115.

Bohmer, R., et al., "Selectively increased growth of fetal hemoglobin–expressing adult erythroid progenitors after brief treatment of early progenitors with transforming growth factor beta." Blood, May 1, 2000; 95(9):2967–2974.

* cited by examiner

METHOD FOR STIMULATING THE PRODUCTION OF FETAL HEMOGLOBIN PRODUCING ERYTHROID CELLS

RELATED APPLICATION

This application claims priority to provisional patent application U.S. Ser. No. 60/149.815, filed Aug. 19, 1999, which is incorporated herein by reference in its entirety.

FIELD OF THE INVENTION

The present invention relates generally to a method for treatment of β-hemoglobinopathies. More specifically, this invention relates to the treatment of β-hemoglobinopathies by administering a composition that promotes an increase in the relative amount of fetal erythropoiesis.

BACKGROUND OF THE INVENTION

Normal adult hemoglobin comprises four globin proteins, two of which are alpha (α) proteins and two of which are beta (β) proteins. During fetal development in mammals (particularly in humans) the fetus produces a fetal hemoglobin which comprises two gamma (γ)-globin proteins instead of the two β-globin proteins. At some point during fetal development or infancy, depending on the particular species and individual, there is a globin switch wherein the erythrocytes in the fetus switch from making predominantly γ-globin to making predominantly β-globin. The developmental switch from production of predominantly fetal hemoglobin (HbF, $α_2γ_2$) to production of adult hemoglobin (HbA, $α_2β_2$) occurs beginning at about 28 to 34 weeks of gestation and continues shortly after birth until HbA becomes predominant. This switch results primarily from decreased transcription of the gamma-globin genes and increased transcription of beta-globin genes. The blood of a normal adult contains only about 2% HbF.

Peripheral blood contains clonogenic cells that produce erythroid colonies and bursts in semisolid culture, given the appropriate combination of growth factors. Individual cells in such colonies can accumulate fetal hemoglobin (HbF), adult hemoglobin (HbA) or a combination of both. The pattern of hemoglobin expression and accumulation is different in cultures from fetal and adult blood. In cultures from adult blood, nucleated red cells accumulate either HbA (F−A+) only or a combination of HbF and HbA (F+A+). Papayannopoulou, et al., *Science* 199: 1349–1350 (1978); Migliaccio, et al., *Blood* 76: 1150–1157 (1990). Individual colonies contain both F+ and F− cells, indicating that both types are progeny from the same circulating stem cells. Thus, during the early stages of development in culture, cells execute an option whether or not to express HbF. The proportion of adult F+ cells developing in culture does not appear to be preprogrammed in vivo, but appears to depend on culture conditions: A shift into the combined HbF and HbA expression pathway can, for example, be achieved in vitro by high serum concentrations, due to the activity of an unidentified compound that can be absorbed on activated charcoal. Bohmer, et al., *Prenatal Diagnosis* 19: 628–636 (1999); Migliaccio, et al., *Blood* 76: 1150 (1990); Rosenblum, et al., in: *Experimental Approaches for the Study of Hemoglobin* 397 (1985).

Hemoglobinopathies encompass a number of anemias of genetic origin in which there is a decreased production and/or increased destruction (hemolysis) of red blood cells (RBCs). There are genetic defects that result in the production by the body of abnormal hemoglobins with a concomitant impaired ability to maintain oxygen concentration. Some such disorders involve the failure to produce normal β-globin in sufficient amounts, some involve the failure to produce normal β-globin entirely. These disorders associated with the β-globin protein are referred to generally as β-hemoglobinopathies. For example, β-thalassemias result from a partial or complete defect in the expression of the β-globin gene, leading to deficient or absent HbA; sickle cell anemia results from a point mutation in the β-globin structural gene, leading to the production of an abnormal (sickled) hemoglobin (HbS).

Sickle cell anemia (sickle cell disease, SCD) is an inherited, chronic, hemolytic anemia characterized by sickle-shaped RBCs. Because deoxygenated HbS is much less soluble than deoxy HbA, it forms a semisolid gel of rod-like tactoids, causing the RBCs to assume a sickle shape. HbS RBCs are more fragile than normal RBCs and hemolyze more readily, leading eventually to anemia.

It has been observed that certain populations of adult patients with beta chain abnormalities have higher than normal levels of fetal hemoglobin (HbF) and have been observed to have a milder clinical course of disease than patients with normal adult levels of HbF. For example, a group of Saudi Arabian sickle-cell anemia patients who express 20–30% HbF have only mild clinical manifestations of the disease. Pembrey, et al., *Br. J. Haematol.* 40: 415–429 (1978). There are also a variety of distinct genetic mutations that cause hereditary persistence of HbF, in which gamma-globin gene expression is not downregulated during development. This condition has been shown to significantly decrease the severity of sickle cell anemia or β-thalassemia in individuals simultaneously affected with both traits. Wood and Weatherall, *Biochem J.* 215: 1–10 (1983). It is now accepted that hemoglobin disorders, such as sickle cell anemia and the β-thalassemias, are ameliorated by increased HbF production. Reviewed in Jane and Cunningham *Br. J. Haematol.* 102: 415–422 (1998). See, also, Bunn, *N. Engl. J. Med.* 328: 129–131 (1993).

While the developmental switch from gamma—to beta— globin gene expression is strictly controlled, there is evidence that external factors can influence gamma-globin gene expression. For example, a delay in the fetal to adult hemoglobin switch has been observed in infants of diabetic mothers, suggesting an affect by circulating physiological factors. Perrine, et al., *N. Engl. J. Med.* 312: 334–338 (1985). Additionally, the ability to enhance HbF synthesis in vivo by pharmacological manipulation was demonstrated in baboons treated with 5-azacytidine (5-AzaC). DeSimone, et al., *Proc. Natl. Acad. Sci, USA* 79: 4428–4431 (1982). Subsequent studies confirmed the ability of 5-AzaC to increase HbF in patients with β-thalassemia and sickle cell disease. Ley, et al., *N. Engl. J. Medicine*, 307: 1469–1475 (1982), and Ley, et al., *Blood* 62: 370–380 (1983).

Other agents that stimulate HbF in vivo include hydroxyurea [Carache, et al., *N. Engl. J. Med.* 332: 1317–1322 (1995)], butyrates [Perrine, et al., *N. Engl. J. Med.* 328: 81–86 (1993); Perrine, et al., *Am. J. Pediatr. Hematol. Oncol.* 16: 67–71 (1994)], activin and inhibin (U.S. Pat. No. 4,997,815), and various organic acids (e.g. valeric, polyhydroxy-benzoic, phenylacetic, mandelic) See, e.g., U.S. Pat. Nos. 5,366,996 and 5,700,640. Although these agents act via mechanisms that are not yet completely understood, it is thought that they partially derepress gamma-globin gene expression, leading to increased levels of HbF.

The effectiveness of many of these therapeutic agents has been demonstrated in several clinical trials, but is limited by unwanted side effects and variability in patient responses. Jane and Cunningham, *Br. J. Haematol.* 102: 415–422 (1998); Olivieri, *Seminars in Hematology* 33: 24–42 (1996). For example, very high dosages of butyric acid are necessary for inducing gamma-globin gene expression, requiring catheritization for continuous infusion of the compound. Moreover, these high dosages of butyric acid can be associated with neurotoxicity and multiorgan damage. Blau, et al., *Blood* 81: 529–537 (1993). There are also limitations to the therapeutic use of hydroxyurea; potential long-term consequences of treatment with this compound include teratogenic and oncogenic effects. While even minimal increases in HbF levels are helpful in sickle cell disease, β-thalassemias require a much higher increase that is not reliably, or safely, achieved by any of the currently used agents. Olivieri, *Seminars in Hematology* 33: 24–42 (1996).

Thus, a need remains in the art for additional, novel, therapeutic methods for treatment of β-hemoglobinopathies—with reduced toxicity—capable of sustained induction of HbF.

SUMMARY OF THE INVENTION

The present invention provides a method for ameliorating β-globin disorders in a mammal. In one aspect of the invention, the treatment involves ex vivo treatment of early erythroid progenitor cells that leads to an increase in the relative amounts of cells subsequently expressing and accumulating HbF. The cell treatment is to be followed by transplantation of the modified cells. In another aspect of the invention, the same modification of progenitor cells occurs in vivo. Both treatments are based on the novel discovery that the modification can be performed very early in the erythroid maturation process, without disturbance of the subsequent proliferation and maturation of the erythrocyte. The present invention also provides a procedure for the monitoring of β-globinopathies and the response of a patient to treatment. In this aspect of the invention, erythropoiesis of a patient is studied (in vivo or in vitro) by generating profiles of correlated contents of different types of hemoglobin present in nucleated red cells (e.g. HbA vs. HbF, HbF vs. HbS, or HbS vs. HbA profiles).

BRIEF DESCRIPTION OF THE DRAWINGS

FIG. 10 is a graph demonstrating that cells programmed to turn into F–A+ cells are being suppressed earlier in the culture phase compared to cells programnmed to become F+ cells. Cultures of adult mononuclear blood cells were seeded with TGF-beta1 (10 ng/$_m$l) and re-seeded in the absence of TGF-beta on the day indicated. On day 8, the absolute numbers of F+ and F–A+ cells were determined and normalized to the values without TGF-beta treatment.

DETAILED DESCRIPTION OF THE INVENTION

Figure 1:
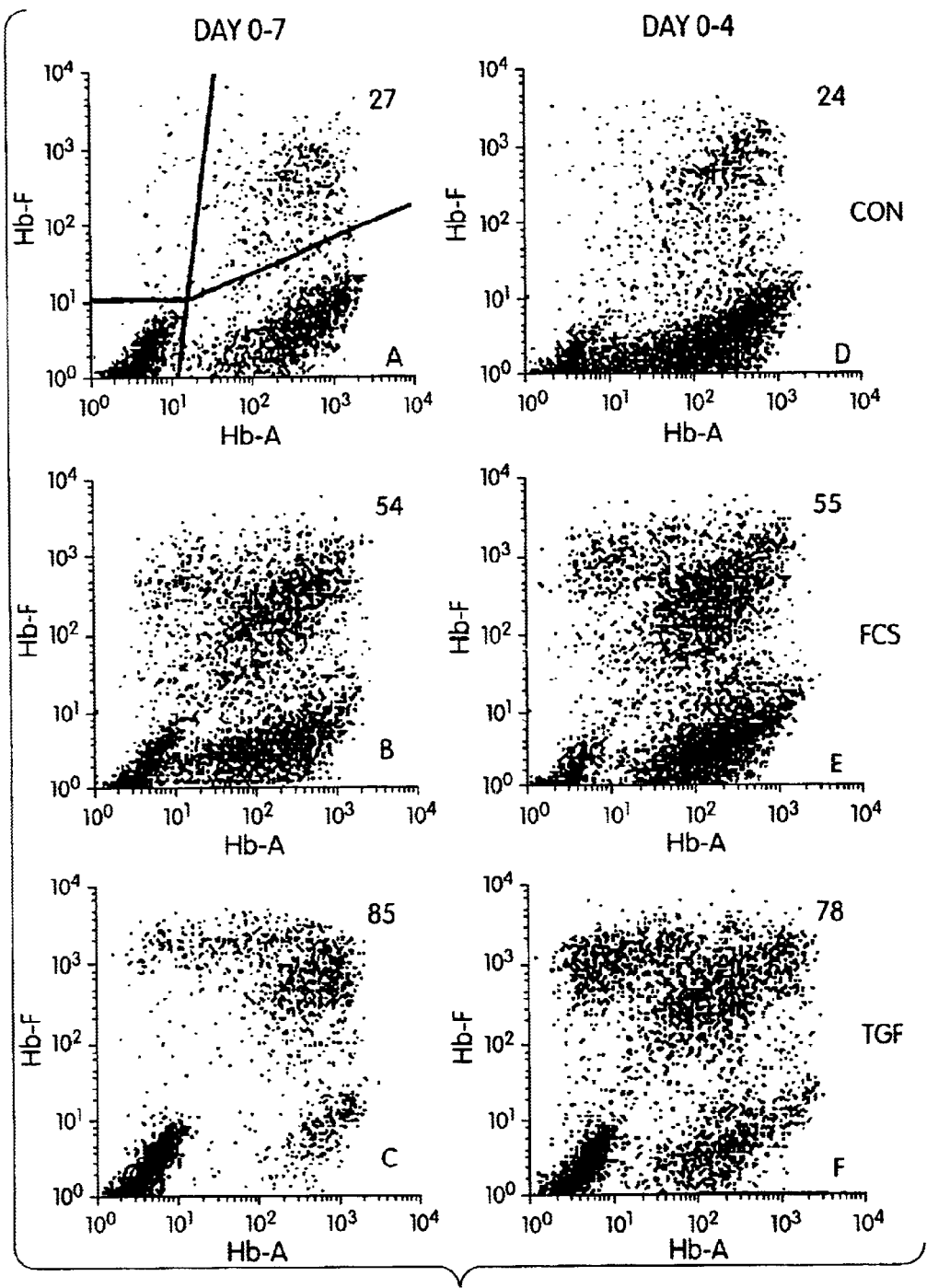
FIG. 1 depicts two-color flow cytometry profiles of correlated cellular hemoglobin contents after treatment with 30% FCS or 10 ng/ml rhTGF-beta 1. Comparison between continuous exposure (day 0–7, left column, graphs A, B, C) and exposure for the first 4 days of culture (day 0–4, right column, graphs D, E, F). Analysis was on day 7 of culture. Cultures were mixed into single-cell suspensions and the correlated contents of HbF and HbA for each individual cell measured by. Each analyzed cell sample results from a mixture of about 100 colonies. Each profile results from 10,000 intact nucleated cells with normal DNA content, gated by Hoechst fluorescence. The proportions of F+ cells (percent of all Hb+ cells) are indicated in the upper right corner of each profile.

The present invention provides a method for ameliorating β-globin disorders in a mammal by treatment of patients with their own stem cells, or other, immunologically compatible stem cells, modified to generate increased proportions of HbF cells. The HbF initiation methods described herein are based on the discovery that there is a narrow time window early after mitogenic stimulation of quiescent cells (between day 2 and day 4 in culture) where said modification takes effect. Due to the HbF initiation early in the differentiation cascade, initiated stem cells retain the potential to produce large numbers of mature red blood cells.

In one aspect of the invention, the treatment involves ex vivo stimulation of HbF production, followed by transplantation of stimulated cells. In this procedure, a patient's hemopoietic stem cells are cultured with the appropriate cytokines, according to procedures well-known in the art (e.g., density gradient centrifugation followed by optional CD34+ enrichment and placement of the stem cell preparations into a standard hemopoietic cell culture medium). In one embodiment of the invention, the stem cells are collected from the umbilical cord blood of a β-globinopathy patient at birth. In another embodiment, the source of stem cells is peripheral blood collected at later stages of a patient's life. In yet another embodiment of the present invention, the stem cells are collected from the bone marrow of a patient. While the use of autologous stem cells is preferable, the methods of this invention include the use of stem cells from other sources that are immunologically compatible.

The cultured stem cells are exposed to an agent that causes an increase in the proportions of cells expressing and accumulating HbF, by mechanisms not yet fully understood. They may include a reversal of the hemoglobin switch or a selective elimination of cells programmed to express only HbA. In one embodiment, the agent is a preparation of human cord serum, either preferentially derived from the patient at birth, or from other sources. This serum is specifically treated as described. In another embodiment, the agent is recombinant TGF-beta1, 2 or 3. The in vitro-treated cells are immature enough to re-populate bone marrow and contribute to the patient's erythropoiesis upon transplantation. In one aspect of the invention, the cells are transplanted directly upon removal from culture. In another aspect of the invention, prior to hematopoietic reconstitution, the cells are cryopreserved according to techniques common in the art, such as describe in U.S. Pat. No. 5,192,553.

In another aspect of the invention, the stimulation of HbF production occurs in vivo. An agent capable of modifying F+ cell proportions is injected into a β-hemoglobinopathy patient. In one embodiment of this invention, TGF-beta is injected into the patient. This treatment is performed at suitable intervals that do not suppress the patient's overall hemopoiesis. In another embodiment in vivo small molecule derivatives of TGF-beta, or an agent having properties similar to TGF-beta, or parts of such derivatives, trigger the receptors and subsequent responses that are responsible for the mechanism by which TGF-beta causes the HbF increase. Such derivatives of TGF-beta may have decreased side effects, i.e., specific beneficial and non-beneficial effects of TGF-beta may be dissociated since TGF-beta appears to have many receptors with different activities. TGF-beta is generally present in body tissues in abundance. It is, however, normally present in a latent, deactivated form through its association with other molecules, such as latency-associated peptide (LAP). TGF-beta may become activated in tissues on demand. Thus, in another aspect of the invention, rather than injecting active TGF-beta, latent TGF-beta in body tissues may be activated by the injection of a specific agent into a patient. Such agent may, for example, be one that dissociates a latency-associated peptide (LAP) from TGF.

The present invention also provides a procedure for monitoring β-globinopathies and the response of a patient to treatment. In this aspect of the invention, erythropoiesis of a patient is studied in vitro or in vivo by generating flow cytometric profiles of correlated contents of different types of hemoglobin present in the nucleated or non-nucleated red blood cells (e.g. HbA vs. HbF; HbF vs. HbS; or HbS vs. HbA profiles). Bohmer, et al., *Br. J. Haematol.* 103: 351–360 (1998).

Example 1

Two-Parameter Flow Cytometry

The present invention is directed to a novel method of quantitative two-color flow cytometry of fluorescently labeled cells. Cells are labeled simultaneously with different fluorescence-conjugated antibodies specific to the type(s) of hemoglobin present in the cell. Antibodies to HbF (gamma-globin chain), HbA (beta-globin chain), and to HbS (-beta-globin chain with the sickle mutation) are used. The profiles of correlated hemoglobin contents are analyzed. This method provides information not available with single-parameter hemoglobin measurements. Bohmer, et al., *Prenatal Diagnosis*, and *Br.J.Haematol.*

1.1 Cell Labeling

Cells are fixed with 5% formaldehyde in PBS at 37° C. for 1 h, exposed to 100% methanol for 5 min at room temperature, then permeabilized in Solution B of the Caltag Fix & Perm kit during incubation with phycoerythrin-conjugated antibodies to the gamma chain of hemoglobin (HbF) (Cortex) and fluorescein isothiocyanate-conjugated antibodies to the beta chain of hemoglobin (HbA) or to fluorescein isothiocyanate-conjugated antibodies specific for sickle cell hemoglobin (HbS) (Isolabs). After incubation, cells are washed and suspended in PBS with 1% formaldehyde and 0.1 µg/ml Hoechst 33342.

1.2 Flow Cytometry

Cells are processed in a Becton-Dickinson Vantage flow cytometer/cell sorter with dual laser excitation (UV and 488 nm). Intact nucleated cells are selected by gating on UV-excited Hoechst 33324 fluorescence (430 nm) which yielded DNA histograms as well as cell cycle information by BudR-induced fluorescence quenching. Bohmer, *Cell Tissue Kinet.* 12: 101–110 (1979). Phycoerythrin (PE) and Fluorescein isothiocyanate (FITC) are excited at 488 nm and measured at 530 nm and 575 nm, respectively. Correlated fluorescence values are recorded with appropriate color compensation. The accuracy of color compensation over 4 logs of fluorescence values is limited. To obtain absolute cell counts from the relative particle counts that a flow cytometer provides, known amounts of fluorescent plastic beads (Coulter Immunobrite Level IV) are added to the cell suspensions. Bohmer, *Cell Tissue Kinet.* 17: 593–600 (1984).

Example 2

Ex vivo Modification of Early Erythroid Stem Cells to Increase the Proportions of Developing F+ Cells 2.1 Cell Culture Blood samples were kept at room temperature and processed as soon as possible (between 2 h and 24 h) after collection. The blood was diluted 1:4 with phosphate buffered saline (PBS), the mononuclear cells isolated by density gradient (density 1.077), washed in PBS with 1% BSA (bovine serum albumin) and cultured without further processing in standard 6-well plates, 3–5 ml per well, at a maximum density of 0.3 million/ml. The standard medium (referred to as "control" medium) comprised a mixture of 2/3 Iscoves MDM and 1/3 RPMI1640, containing methylcellulose (0.9%), C—CHS (1%), EPO (1 U/ml), SCF (20 ng/ml), IL3 (10 ng/ml), insulin (3 $\mu$g/ml), iron-saturated transferring (70 $\mu$g/ml), mercaptoethanol (0.7 nM). Cytokines were from R&D Systems, Minneapolis, Minn. or Genzyme, Cambridge, Mass.

2.2 Autologous Serum Preparation

Human cord blood was collected without anticoagulant, the clots removed, the remaining blood centrifuged at 3000 rpm for 20 min., and the supernatant serum was collected. Approximately 10 ml is a suitable quantity of serum for one cell culture treatment. The serum was extracted twice with 3 volumes (ca. 30 ml) of chloroform. This removes toxic substances and allows the serum to be used at high concentrations.

2.3. Cell Culture Treatment with Serum

On day 1 or day 2 of culture, the chloroform-extracted serum was added to the stem cell cultures at 30% of the total culture medium volume. After 2 or 3 days of culture (day 4 overall), the cells were removed from the culture and washed. The cells were then ready for transplantation or cryopreservation.

2.4 TGF-beta Treatment of Cultures

Transforming growth factor beta (TGF-beta) was found to be more powerful than serum, when used with the same timing. A relatively brief exposure to TGF-beta during the first few days of cell culture caused a lasting shift towards HbF expression with no reduction in subsequent clonal expansion (see data below). This effect did not depend on the combination of cytokines that were used to stimulate and support erythropoiesis. Mononuclear cells from adult blood were cultured from day 0 to day 4 with 10 ng/ml recombinant human transforming growth factor beta-1, hereinafter referred to as rhTGF-beta-1 or TGF-beta. The most useful concentration of TGF-beta depended on cell density and timing of exposure.

(a) Increase in F+ Cell Proportions by Short-term TGF-beta Treatment

The effect of TGF-beta treatment on cell cultures was examined and compared to the effect of serum. Cultures were incubated with TGF-beta or serum from day 0 to day 4 of culture. On day 4, part of the cultures were washed and re-seeded in control medium without TGF-beta or serum, the other part remained unmodified until the time of harvest. TGF-beta was removed from cultures by washing the cultures twice in PBS/BSA, then re-seeding them in fresh medium. On day 7, cultures containing hundreds of colonies were turned into single-cell suspensions and the correlated contents of HbA and HbF measured by flow cytometry (FIG. 1). In the control cultures, the large majority of nucleated red cells were clustered at high levels of HbA but little or no HbF (F–A+ ). A small proportion (ca. 20% in this case) contained HbF together with HbA (F+ A+ ). Some cells were F+ A– or spread over all areas of the profile. The subdivision of profiles chosen for numerical evaluations is indicated in the first profile. The time course of hemoglobin synthesis in erythroid cultures is discussed in Bohmer, et al., *Br. J. Haematol.* 103: 351–360 (1998), herein incorporated by reference. TGF-beta increased the proportions of F+ cells dramatically, and more so than serum. Four days of exposure to the HbF-inducing agents appeared nearly as effective as continuous exposure up to the day of analysis (day 7). Continuous TGF-beta treatment, but not the 4-day treatment, resulted in strongly reduced total cell counts, and colonies were much smaller and appeared to contain apoptotic/necrotic cells. Various additional tests showed that the effect of serum is not based on active TGF-beta in serum. The combination of TGF-beta with 30% treated serum gives an even better result than either of the two agents alone, with reduced toxicity and a near 100% F+ population.

(b) Induction of HbF Expression within the First Four Days of Culture

Figure 2:
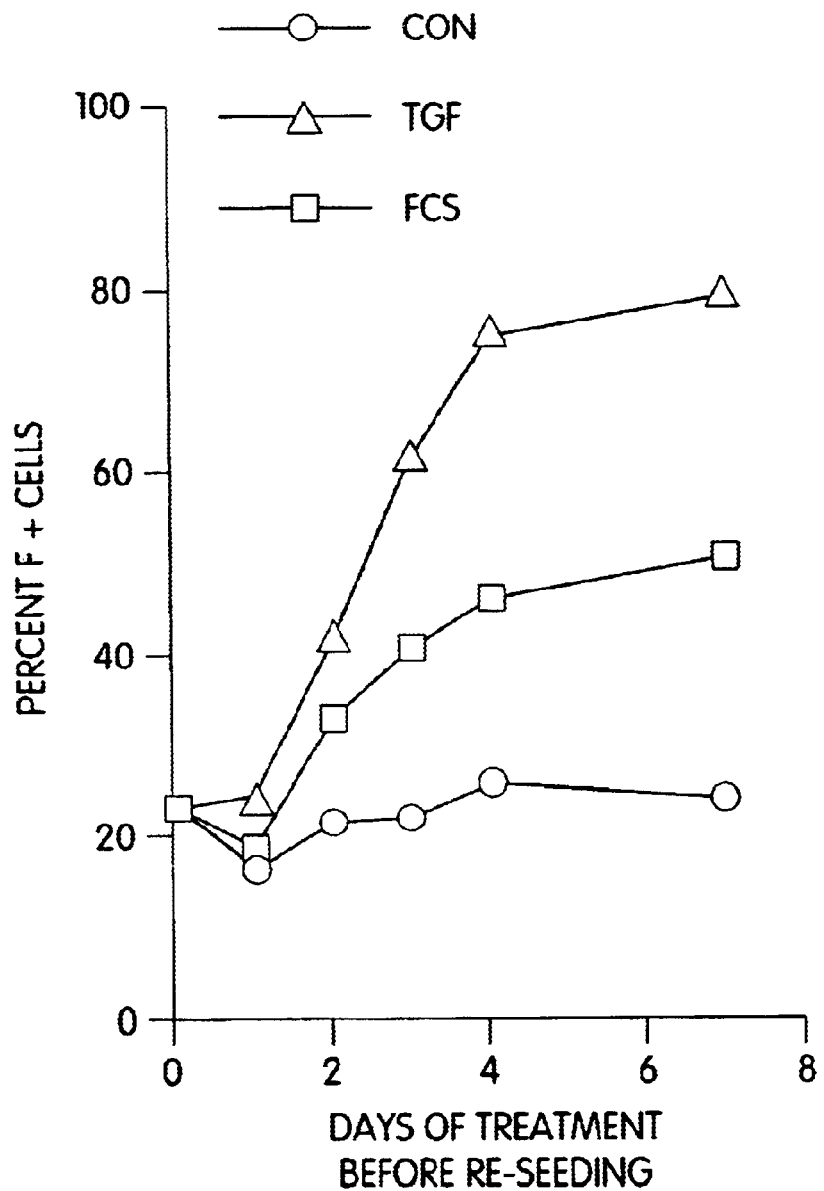
FIG. 2 is a graph showing stimulation of HbF by short-term incubation with FCS or TGF-beta. Cultures initiated in the presence of TGF-beta or FCS were washed and re-seeded in control medium after 0, 1, 3 and 4 days. On day 7 of culture, the proportions of F+ cells were determined as a function of exposure time. Circles: control; squares: FCS; triangles: TGF-beta.

The proportions of F+ cells as a function of time of exposure to TGF-beta are shown in FIG. 2. Also included on this graph are data from cells cultured in 30% fetal calf serum (FCS). The proportions of F+ cells began to increase between days 1 and 2 and nearly leveled out by day 4. The proportions of F+ cells reached a plateau at ca. 50% with FCS and 80% with TGF-beta. The time course of TGF and serum effects were similar.

Figure 3:
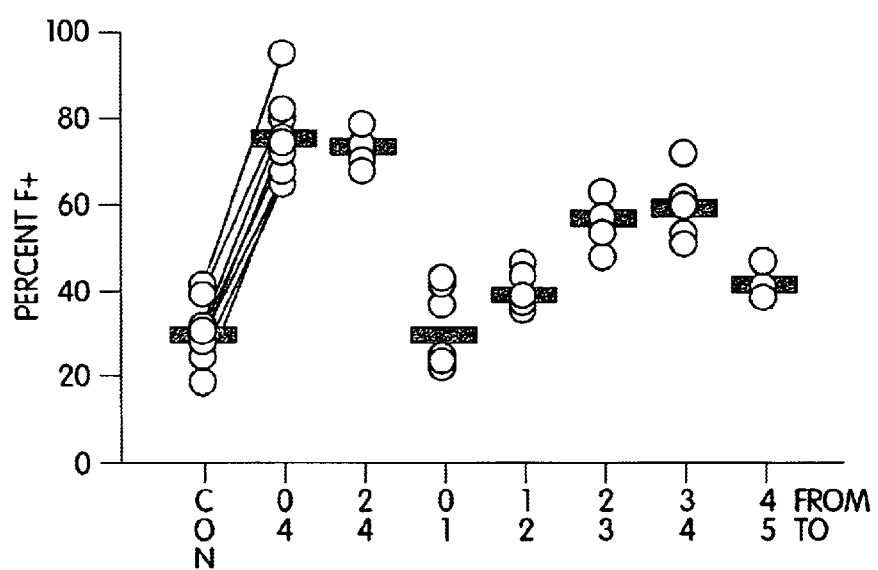
FIG. 3 is a graph depicting the statistics of the effect of TGF-beta 1 on cultures from different donors, comparing various treatment timings between days 0 and 5. The median values are indicated as horizontal bars. Each individual case is displayed by an open circle. In the case of 4-day treatment, data pairs are connected to demonstrate the correlation of variations (r=+0.84). The difference between controls and 4-day TGF-beta treatment is statistically highly significant ($p<0.0001$).

To test if the required exposure time could be further narrowed, cultures were exposed to TGF-beta for only 1 day during the first 5 days of culture (FIG. 3). Following exposure for only one day between days 2 and 4, the proportions of F+ cells were substantially increased and only slightly less than after exposure from day 0 to day 4.

(c) F+ Cell Proportions at the Later Culture Phase

Figure 4:
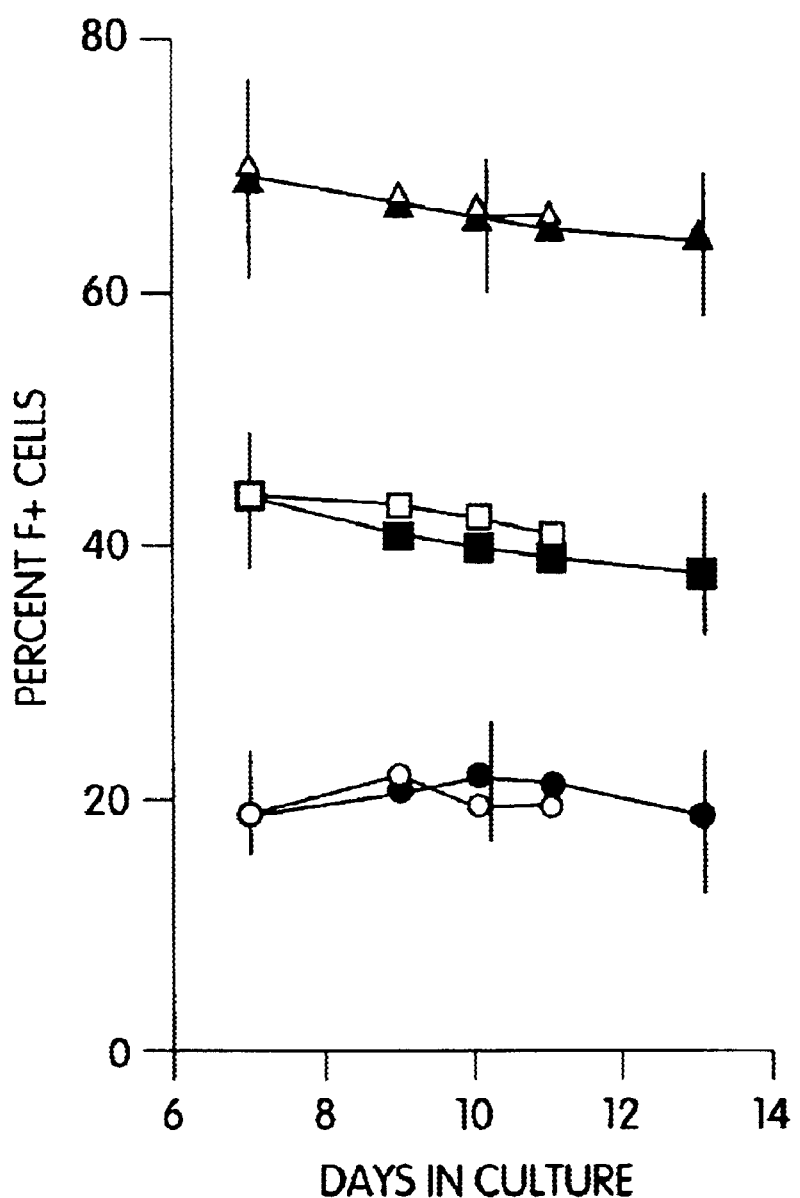
FIG. 4 depicts a graph of the proportions of F+ cells at a later culture phase. Cultures were incubated with TGF-beta or FCS for 4 days, then washed and re-seeded in fresh control medium. On days 7 and 10, the cultures were further diluted in fresh control medium (closed symbols) or medium supplemented with TGF-beta 1 (open symbols). The percent F+ cells were determined at selected times between day 7 and day 13. The time course is shown from one experiment were all conditions were investigated together on the cells from the same donor. Part of this experiment was repeated 3 more times, comparing day 0–4 TGF-beta treatment and control. The ranges of resulting F+ proportions, measured on days 7, 10 and 13, are indicated in the figure as vertical bars. Circles: control; squares: FCS; triangles: TGF-beta.

The proportions of F+ cells during further culture development were monitored in a separate experiment (FIG. 4). After a 4-day treatment with TGF-beta or serum, cultures were grown in control medium and again re-seeded on days 7 and 10, each time with a 10-fold dilution, to minimize the exhaustion of medium components by the rapidly expanding cell mass. The increased proportions of F+ cells, as introduced by brief TGF-beta or serum treatment, were maintained during further culture growth without TGF-beta or serum, suggesting that F+ and F–A+ cells expanded at the same rate.

To assess the effect of TGF-beta at this later culture phase, parts of the cultures in the same experiment were newly supplied with TGF-beta beginning on day 7 (data included with open symbols in FIG. 4). When added at this time, TGF-beta had no effect on F+ proportions. However, a complete and lasting growth arrest in the newly developing secondary colonies occurred after approximately 2 days of TGF-beta treatment, mostly at the 8–16-cell stage (data not shown).

(d) Effect of TGF-beta on Absolute Cell Numbers and Long-term Proliferation

The increase in the proportions of F+ cells measured between week 1 and 2 of culture could be due to several different mechanisms, such as a reversal of the hemoglobin switch, a selective proliferative boost to F+ cells, or a selective inhibition of F−A+ cells. If the TGF-beta effect were to be based on purely one of these three mechanisms, it could be distinguished by quantitating absolute, instead of relative, cell numbers. A reversal of the hemoglobin switch would lead to increased numbers of F+ cells at the numerically equal expense of F−A+ cells. A selective increase in the rate of F+ cell proliferation would leave F−A+ cell numbers unchanged. Similarly, a selective suppression of F−A+ cells would leave F+ cell numbers unchanged.

Figure 5:
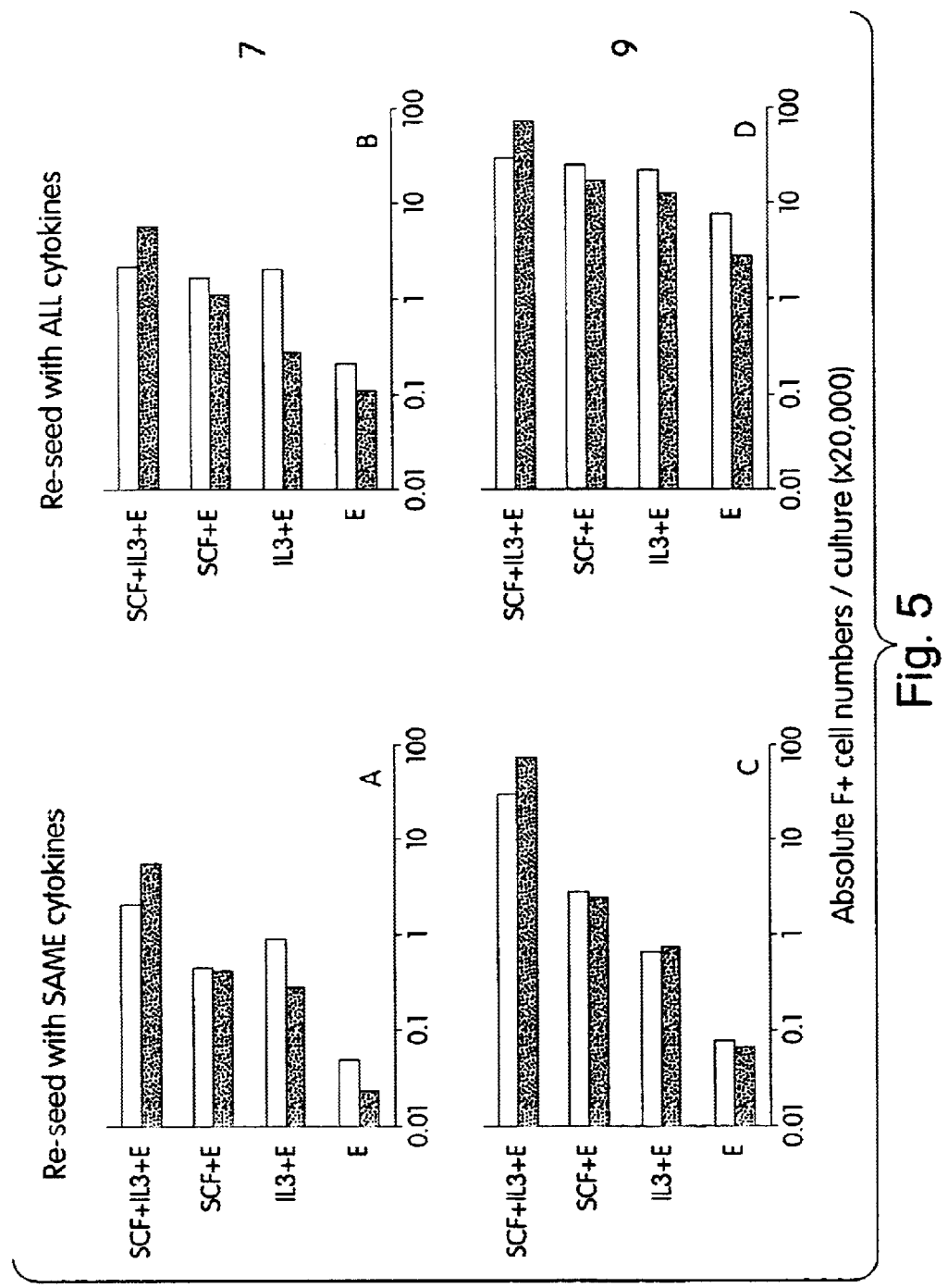
FIG. 5A is an example of a time course from one experiment. Cultures were treated with TGF-beta for 4 days, then propagated without TGF-beta, with further subcultivation and dilution on days 7 (1:10), 10 (1:5) and 13 (1:5). Absolute numbers of F+ and F−A+ cells per culture were determined on days 7, 10, 13 and 16. Total cell numbers were calculated using preceding culture dilution factors in the following manner: at each time of analysis, some of the cells were removed for counting, those that go back into the culture after counting are seeded with a dilution of fresh medium, to avoid medium exhaustion. Therefore, the actual numbers in the plates increase only between seeding and harvest. To calculate cell production over the whole culture time, it is necessary to multiply the counted cell numbers in the plates with all previous culture dilution factors. Closed symbols depict data from F−A+ cells, open symbols show F+ cells, and triangles show TGF-beta-treated cultures, while circles show the controls.
FIG. 5B is a graph indicating the TGF-beta-induced change of total F+ and F− cell numbers, shown as ratio of N(TGF)/N(CON). Cultures were treated with TGF-beta for 4 days., then propagated without TGF-beta, with further subcultivation and dilution on days 7 (1:10), 10 (1:5) and 13 (1:5). Absolute numbers of F+ and F−A+ cells per culture were determined on days 7, 10, 13 and 16. Individual experiments are distinguished by different symbols. Pairs of F+ and F−A+ values are connected to demonstrate positive correlation. Median values are indicated by horizontal bar.
Figure 5A:
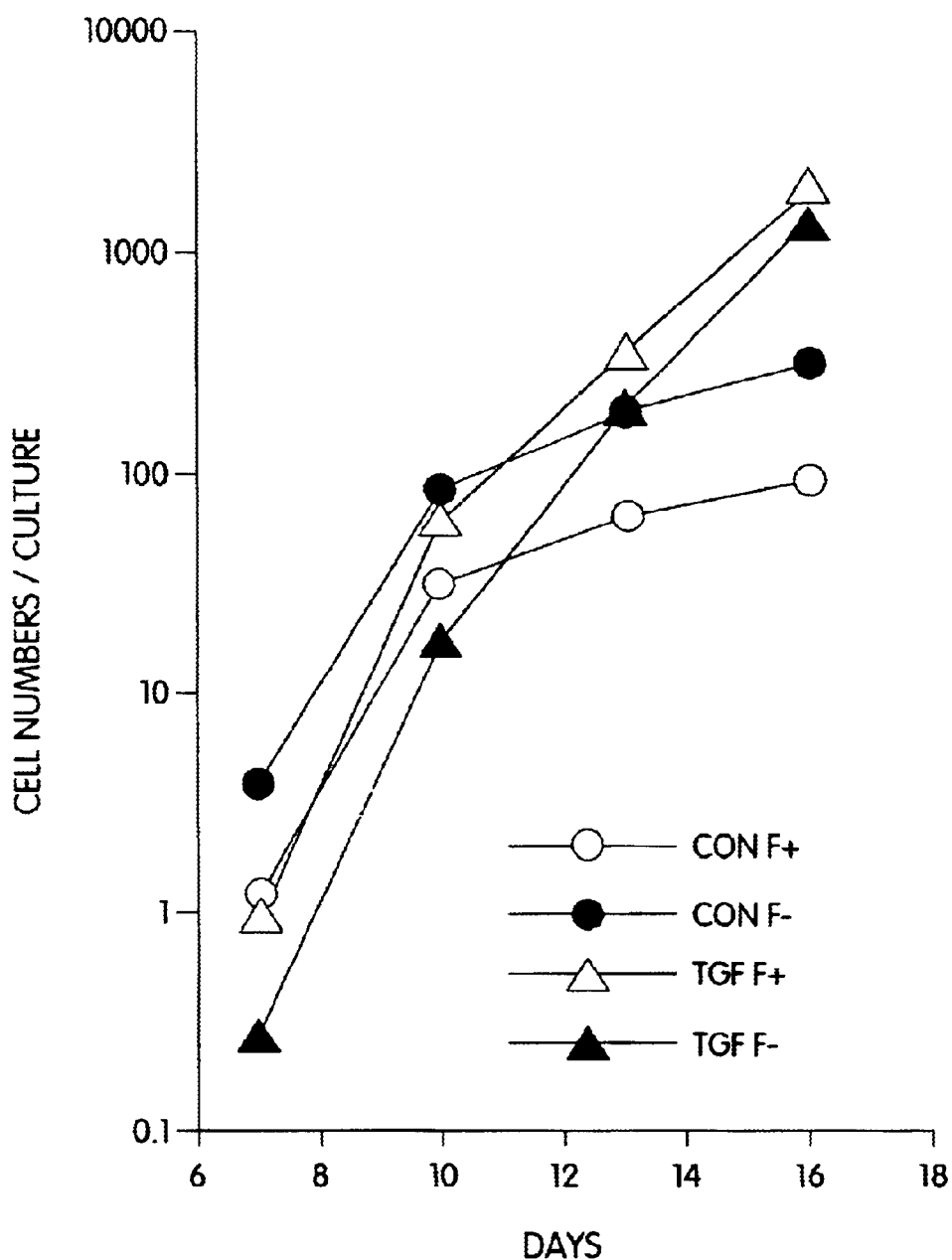

Cultures that were treated with TGF-beta from day 0–4 were sub-cultivated again on days 7, 10 and 13, and the total numbers of F+ and F−A+ cells per culture were determined on days 7, 10, 13 and 16. FIG. 5A shows the time course from a representative experiment. Between days 7 and 10, the total numbers of F+ cells (open symbols) in TGF-beta-treated and control cultures were approximately equal, whereas F−A+ cells (full symbols) were dramatically reduced in the TGF-beta-treated cultures. Between day 7 and 10, both cell types in both cultures proliferated at approximately the same rate. After day 10, in control cultures, the proliferation decreased strongly and equally for both F+ and F−A+ cells, maintaining the ratio. No secondary colonies were seen following the subcultivation on day 13. In contrast, the proliferation in TGF-beta-treated cultures continued for much longer for both F+ and F−A+ cells. The F−A+ cell numbers were gradually reducing the gap with F+ cells, in agreement with the gradually decreasing proportions of F+ cells shown in FIG. 4. The number of days for which the proliferation of TGF-beta-treated cultures could be maintained was highly variable between donors and appeared to correlate with the initial numbers of clonogenic cells per ml of blood. The complete cessation of proliferation around day 13 in untreated control cultures occurred with little variation between donors.

Figure 5B:
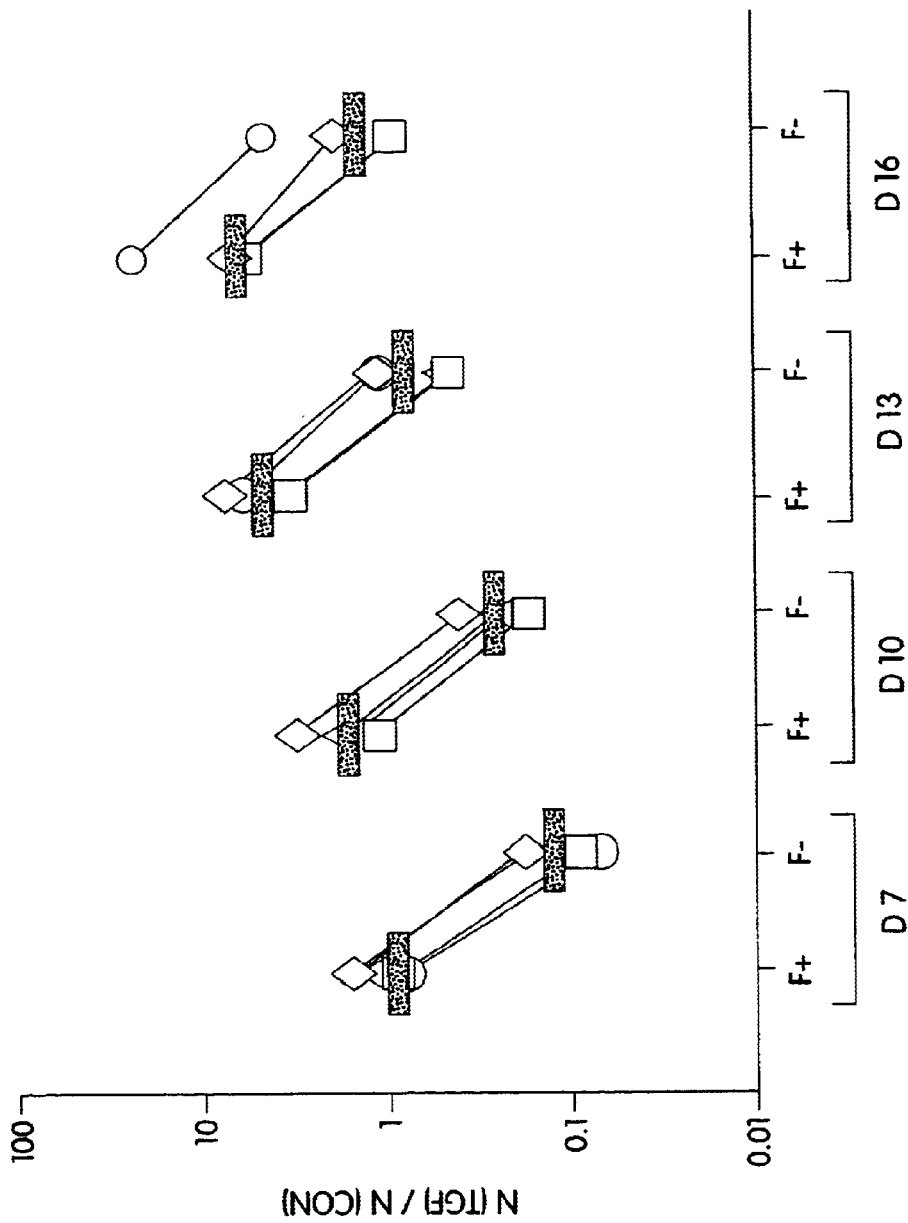

In spite of variations in the exact time course and culture lifespan, both the initial reduction of F−A+ cells and the increase in F+ division potential was strictly reproduced in 4 experiments from different donors, and the data are summarized in FIG. 5B. The ratios of absolute cell numbers in TGF-beta-treated and control cultures (N(TGF)/N(CON)) are shown on different days, with medians indicated as horizontal bars, the pairs of F+ and F−A+ values connected and the 4 individual cases distinguished by symbol. On day 7, the F+ cell numbers were little affected by TGF-beta (ratio=1), whereas the F−A+ cell numbers were reduced ca. 10-fold. The day-7 values are available from 12 additional experiments (not shown), with medians exactly the same as shown here for the 4 experiments where the entire culture lifespan was studied. With increasing culture time, the ratios increased for both F+ and for F−A+ cells, indicating that both types of cells in TGF-beta-treated cultures were able to out-proliferate the controls, as exemplified in FIG. 5A. On average, the F+ population of TGF-beta-treated cultures grew to nearly 10-fold higher levels than the controls. However in 2 (out of 5) experiments, the TGF-beta-treated cultures kept proliferating and producing secondary colonies beyond 3 weeks, with N(TGF)/N(CON) of F+ cells exceeding 100. Under standard culture conditions, this lifespan is usually observed only in cultures from fetal blood at early gestational age.

(e) TGF-beta Induction Does not Depend on the Combination of Cytokines

Figure 6:
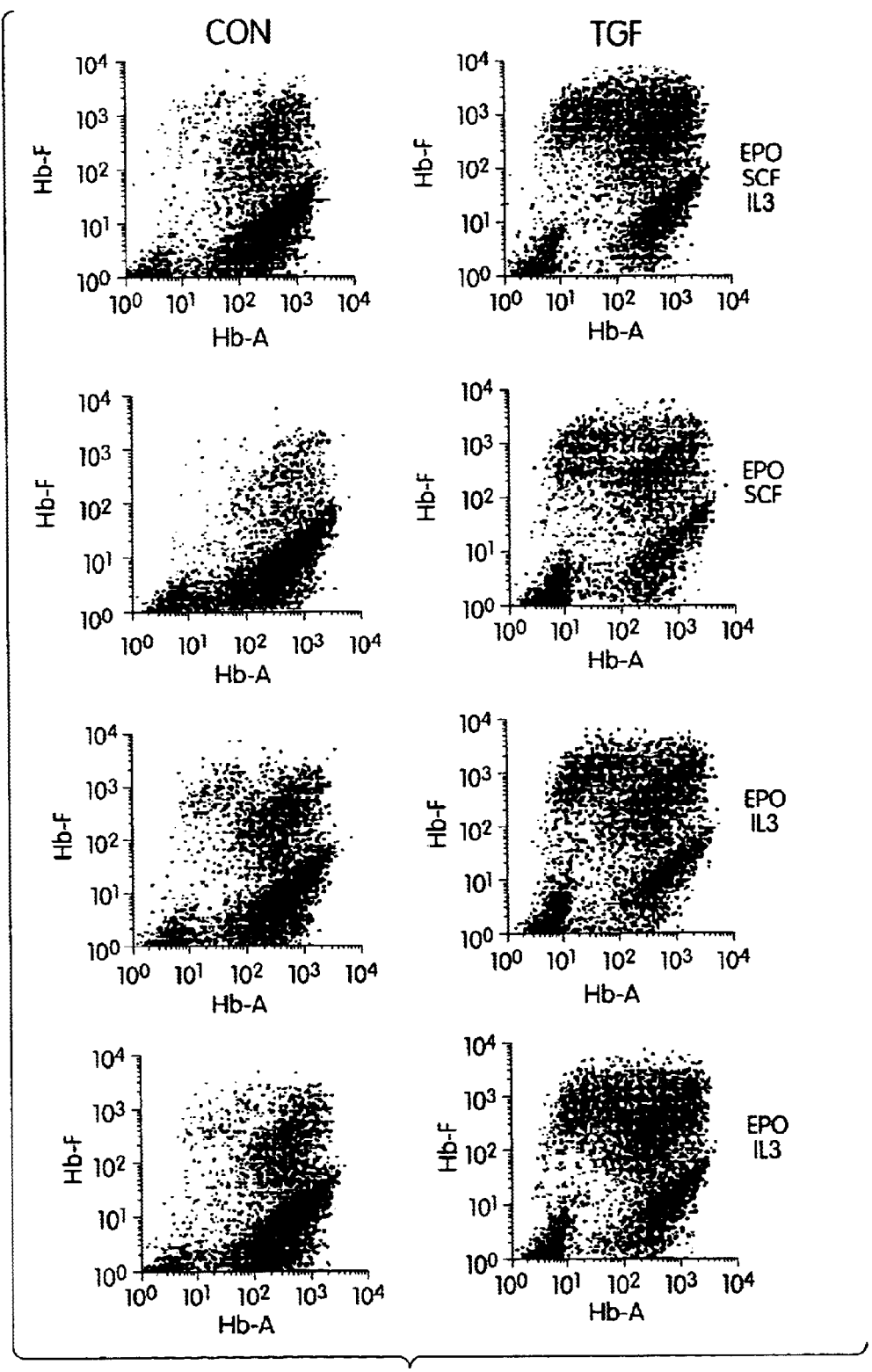
FIG. 6 shows two-color flow cytometry profiles demonstrating the effect of different cytokine combinations on the proportions of F+ cells and the effect of TGF-beta. Cultures were grown in media with combinations of cytokines as indicated on the right side of the profiles, in the presence (TGF) or absence (CON) of TGF-beta. After 4 days, cultures were re-seeded without TGF-beta in fresh media with all three cytokines. Profiles were recorded after 8 days of culture (4 days after re-seeding).

TGF-beta may interact with the signaling mechanisms of cytokines required to support erythropoiesis. The manner in which HbF stimulation by TGF-beta would be affected by different cytokine cocktails that are known to support erythropoiesis less than optimally was examined. Cultures were initiated in EPO+SCF+IL3, EPO+SCF, EPO+IL3 and SCF+IL3, and treated with TGF-beta 1 for the first 4 days. The cultures were then re-seeded, without TGF-beta, in the full cytokine cocktail (EPO+SCF+IL3) and analyzed between days 7 and 9 of culture. FIG. 6 shows examples of the resulting profiles. While the shape of hemoglobin profiles as well as the total numbers of hemoglobinized cells were affected by sub-optimal cytokine combinations, the TGF-beta-induced increase of F+ cells was similar for all conditions.

(f) Minimal Cell Cycle Perturbation During Short-term TGF-beta Treatment

Figure 7:
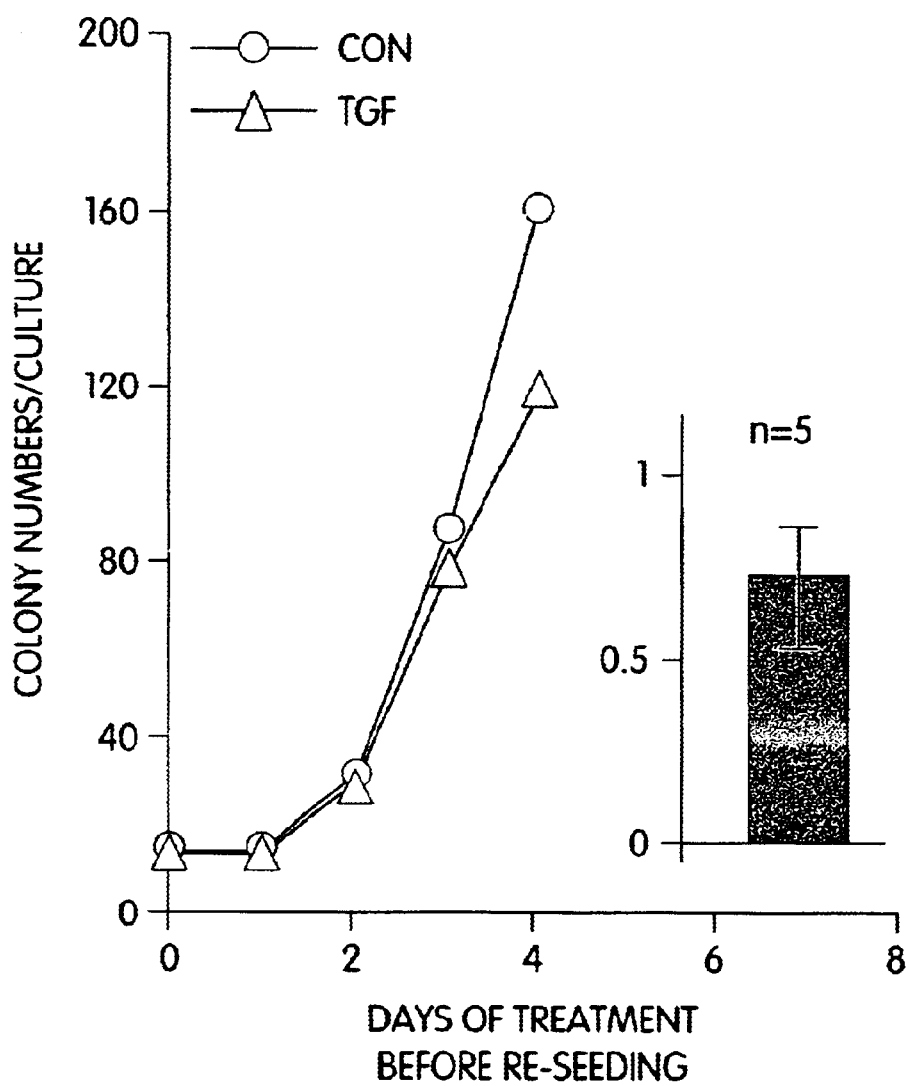
FIG. 7 is a graph demonstrating the effect of TFG-beta on the cell cycle during short-term treatment. Cell cultures were seeded in the presence (TGF) and absence (CON) of TGF-beta and on days 1, 2, 3 and 4 washed and re-seeded in the absence of TGF-beta. On day 9, the secondary colonies/ clusters were counted and plotted as a function of the number of the day of treatment before reseeding. The insert shows the degree of colony reduction [n(TGF)/n(CON)] by 4-day TGF treatment. Statistics from 5 experiments are shown.

To test the cell cycle effect of TGF-beta during the first 4 days of treatment, the numbers of secondary erythroid colonies that developed upon re-seeding the cultures after different duration of TGF-beta exposure were counted (FIG. 7). A decrease in the number of secondary colonies upon re-seeding would reflect a decrease in the number of divisions undergone by colony forming cells before the cultures were re-seeded as a single-cell suspension. However, the secondary colonies became smaller and more numerous, without much effect of TGF-beta. The numbers of secondary colonies began to increase between day 1 and 2, equally in TGF-beta and controls. Between days 3 and 4 the beginnings of inhibition by TGF-beta could be seen. The degree of inhibition (decrease in secondary colony numbers) beginning between day 3 and 4 of TGF-beta exposure was variable between experiments and did not strictly correlate with the resulting proportions of F+ cells. Thus, we do not yet fully control this mechanism. We conclude that TGF-beta did not interfere with cytokine-dependent proliferation during the first few days of treatment.

(g) Relative Effectiveness of Different Forms of TGF-beta

Figure 8:
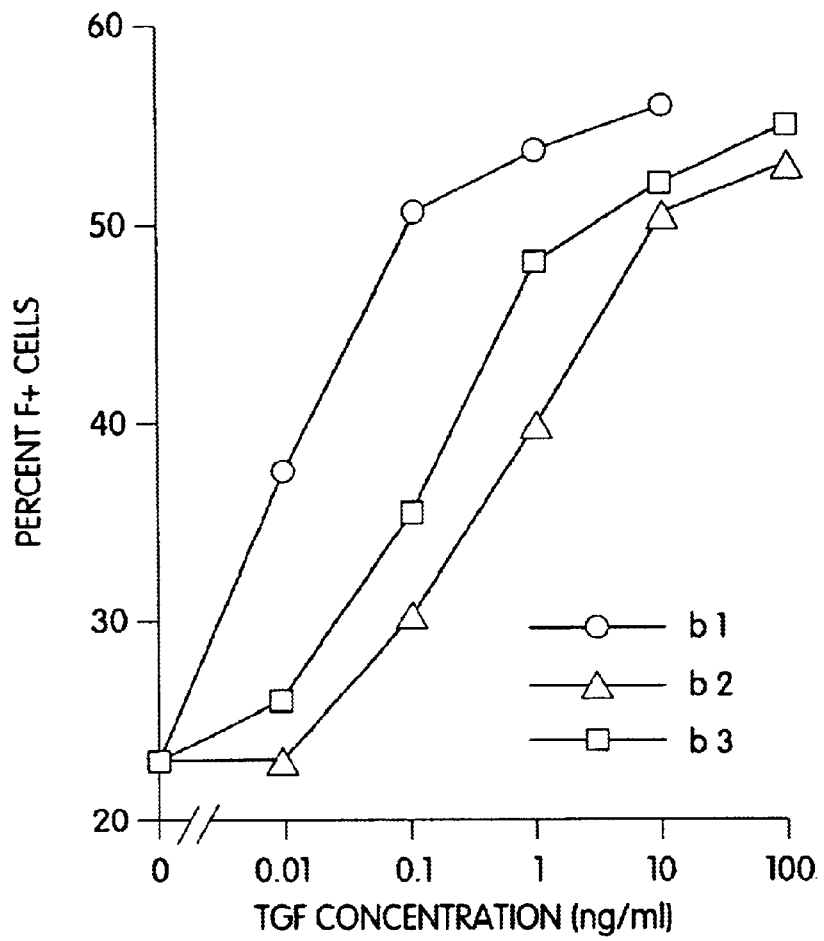
FIG. 8 depicts a graph of titrations of different forms of TGF-beta (beta 1, 2 and 3). Cultures were exposed to TGF-beta 1, 2 and 3 at a wide range of concentrations. On day 4, cultures were re-seeded in control medium, and the proportions of F+ cells were determined on day 7.

To investigate the relative potencies of different forms of TGF-beta to increase the proportions of F+ cells, TGF-beta 1, 2 and 3 were titrated over a wide range of concentrations. The averaged data of two experiments with blood cells from different donors are shown in FIG. 8. For these titrations, treatment began on day 2, the onset of the TGF-sensitive culture phase. At this time (day 2), the titration curves shifted to much lower concentrations compared to treatments from day 0–4. This shift may be due to TGF degradation starting at the time of addition to the culture. TGF-beta 2 was nearly 100 times less effective than TGF-beta 1. The relative potency of TGF-beta 3 was in between TGF-beta 1 and TGF-beta 2.

(h) Effect of TGF-beta and FCS on Sickle Cell Erythropoiesis

Figure 9:
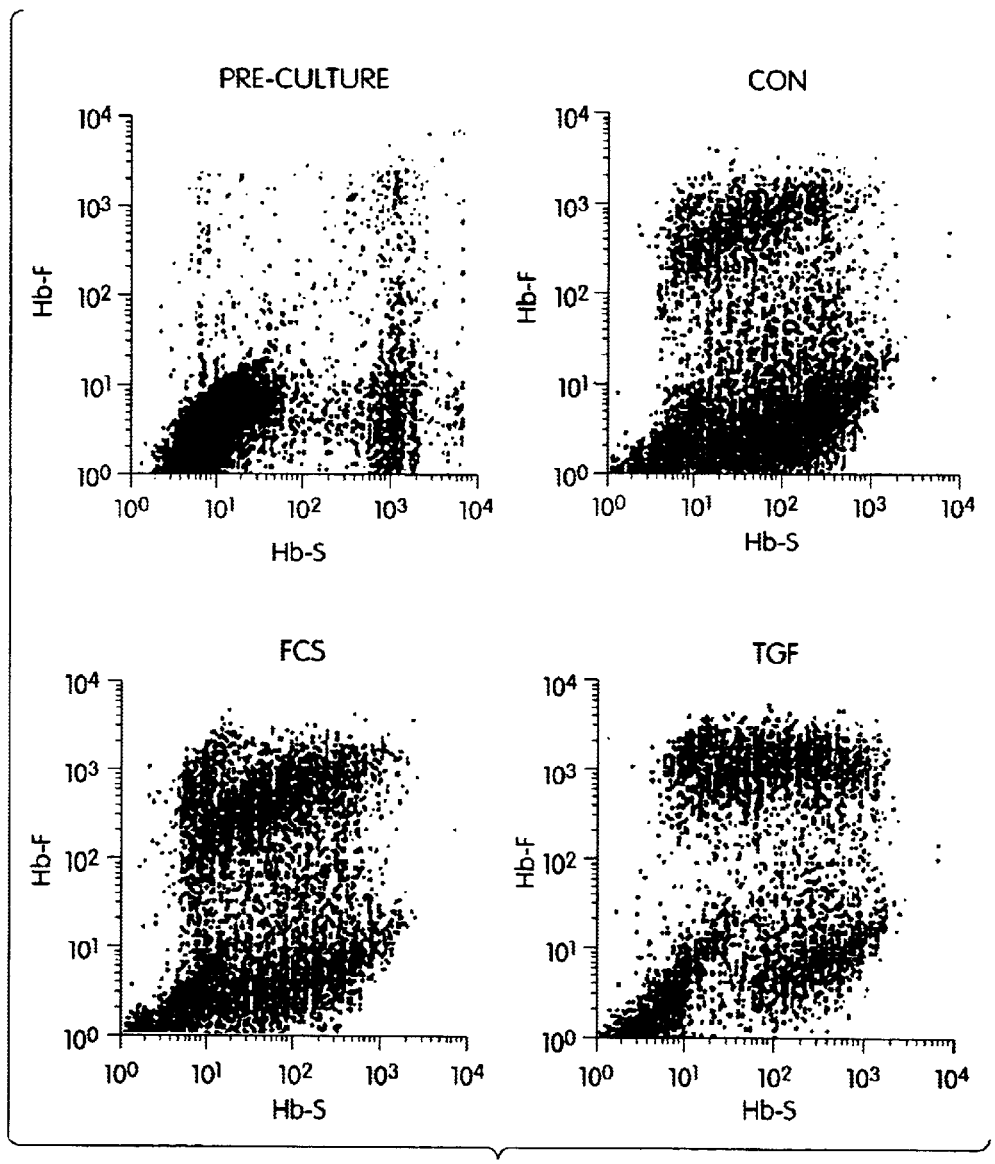
FIG. 9 shows two-color flow cytometry hemoglobin profiles from a sickle cell patient before culture (FIG. 9A) and after 7 days of culture in control medium (FIG. 9B), FCS (FIG. 9C) and TGF-beta (FIG. 9D).

Mononuclear cells from one sickle cell patient were continuously cultured in 30% FCS or 10 ng/ml TGF-beta. The cells were labeled with the same antibodies to HbF but with antibodies specific for HbS instead of HbA. FIG. 9 shows the hemoglobin profiles on day 7 of culture, the profile before culturing is also shown in FIG. 9A, representing nucleated red cells circulating in the peripheral blood of the patient. Both serum and TGF-beta caused an increase in relative F+ cell numbers, similar to the trend seen in normal blood cultures.

EQUIVALENTS

From the foregoing detailed description of the specific embodiments of the invention, it should be apparent that a unique method of treating β-hemoglobinopathies has been described. Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims

What is claimed is:

1. A method for stimulating the production of fetal hemoglobin (HbF) producing erythroid cells, comprising contacting erythroid progenitor cells ex vivo with a cytokine, wherein said cytokine is selected from the group consisting of transforming growth factor-beta 1 (TGF-beta 1), transforming growth factor-beta 2 (TGF-beta 2), and transforming growth factor-beta 3 (TGF-beta 3), and wherein said cytokine is present in an amount sufficient to increase the number of HbF producing erythroid cells compared to adult hemoglobin producing cells.

2. The method of claim 1, wherein said erythroid progenitor cells are obtained from peripheral blood.

3. A method of increasing the proportion of fetal hemoglobin (HbF) producing erythroid cells comprising contacting a population of erythroid progenitor cells ex vivo with a composition comprising a transforming growth factor-beta (TGF-beta1 cytokine, wherein the TGF-beta cytokine is selected from the group consisting of TGF-beta 1, TGF-beta 2, and TGF-beta 3, and wherein said TGF-beta cytokine is present in an amount sufficient to increase the proportion of HbF producing erythroid cells compared to adult hemoglobin producing erythroid cells.

4. The method of claim 3, wherein said erythroid progenitor cells are obtained from peripheral blood.

5. The method of claim 3, further comprising isolating the resultant HbF-producing erythroid cells.

* * * * *